United States Patent
Russell

(10) Patent No.: US 10,272,107 B2
(45) Date of Patent: Apr. 30, 2019

(54) METHOD FOR TREATING INFLAMMATORY BRAIN DISORDERS AND TRAUMATIC BRAIN INJURY

(71) Applicant: Kenneth O. Russell, Austin, TX (US)

(72) Inventor: Kenneth O. Russell, Austin, TX (US)

( * ) Notice: Subject to any disclaimer, the term of this patent is extended or adjusted under 35 U.S.C. 154(b) by 0 days.

(21) Appl. No.: 15/695,188

(22) Filed: Sep. 5, 2017

(65) Prior Publication Data

US 2019/0070218 A1 Mar. 7, 2019

(51) Int. Cl.
| | |
|---|---|
| *A61K 33/24* | (2019.01) |
| *A61K 33/06* | (2006.01) |
| *A61K 31/51* | (2006.01) |
| *A61P 25/28* | (2006.01) |
| *A61K 31/593* | (2006.01) |
| *A61K 45/06* | (2006.01) |
| *A61K 31/714* | (2006.01) |

(52) U.S. Cl.
CPC .............. *A61K 33/24* (2013.01); *A61K 31/51* (2013.01); *A61K 31/593* (2013.01); *A61K 31/714* (2013.01); *A61K 33/06* (2013.01); *A61K 45/06* (2013.01); *A61P 25/28* (2018.01)

(58) Field of Classification Search
None
See application file for complete search history.

(56) References Cited

U.S. PATENT DOCUMENTS

| | | | | |
|---|---|---|---|---|
| 2002/0086067 | A1* | 7/2002 | Choi | A61K 31/352 424/729 |
| 2008/0027032 | A1* | 1/2008 | Gimona | A61K 31/365 514/161 |
| 2008/0181937 | A1* | 7/2008 | Fotuhi | A61K 9/7023 424/449 |
| 2008/0317885 | A1* | 12/2008 | Baker | A61K 31/192 424/739 |
| 2010/0178362 | A1* | 7/2010 | Komorowski | A61K 33/24 424/655 |
| 2011/0065662 | A1* | 3/2011 | Rinsch | A61K 31/352 514/33 |
| 2016/0303160 | A1* | 10/2016 | Bienkiewicz | A61K 31/714 |
| 2017/0027902 | A1* | 2/2017 | Robertson | A61K 31/232 |
| 2018/0028482 | A1* | 2/2018 | Prasad | A61K 31/216 |

OTHER PUBLICATIONS

Jung, H., et al., Biol. Pharm. Bull. 32(8): 1433-1438. (Year: 2009).*

* cited by examiner

*Primary Examiner* — David J Blanchard
*Assistant Examiner* — Daniel F. Coughlin
(74) *Attorney, Agent, or Firm* — Frank Huy Pham; Pham IP Group

(57) ABSTRACT

The present invention provides methods for treating an inflammatory brain disease and for treating a traumatic brain injury in a human having an inflammatory component applying transdermal pharmaceutical compositions comprising chromium, magnesium, and thiamine as active ingredient compounds that act as neuroprotective iron chelators and brain glucose-uptake enhancement that are suitable for the treatment of traumatic brain injury. The invention further relates to methods of delivering the pharmaceutical compositions that target the brain and/or central nervous system certain novel iron chelators of the type described in the specification.

7 Claims, No Drawings

METHOD FOR TREATING INFLAMMATORY BRAIN DISORDERS AND TRAUMATIC BRAIN INJURY

The present application is a Continuation In-Part application of the U.S. Pat. No. 9,585,898 file on Feb. 11, 2008, to Kenneth O. Russell, entitled "METHOD FOR THE REDUCTION OF DANGEROUS BLOOD SUGAR LEVELS", each in their entirety incorporated herein by reference.

FIELD OF USE

The invention relates to peptides useful for treating inflammatory brain disorders, including, but not limited to traumatic brain injury.

BACKGROUND

1. Traumatic Brain Injury

Traumatic brain injury (TBI) is caused by a head injury that can result in lasting damage to the brain and affects up to 10 million patients worldwide each year. The health effects of TBI can be debilitating, result in long term disability, and have significant financial burdens.

Traumatic brain injury is caused by an external mechanical force, such as a blow to the head, concussive forces, acceleration-deceleration forces, or a projectile. It may occur both when the skull fractures and the brain is directly penetrated (open head injury) and also when the skull remains intact but the brain still sustains damage (closed head injury).

Symptoms of a TBI range in severity, depending on the extent of damage to the brain, and may include headaches, neck pain, confusion, difficulty remembering, concentrating, or making decisions, dizziness, fatigue, mood changes, nausea, irritability, photophobia, blurred vision, ringing in the ears, loss of sense of taste or smell, seizures, sleep disturbances, hypoxemia, hypotension and brain swelling, muscle weakness, paralysis, coma, and a progressive decline in neurologic function following the traumatic brain injury.

TBI is graded as mild (meaning a brief change in mental status or consciousness), moderate, or severe (meaning an extended period of unconsciousness or amnesia after the injury) on the basis of the level of consciousness or Glasgow coma scale (GCS) score after resuscitation. The GCS scores eye opening (spontaneous=4, to speech=3, to pain=3, none=0, motor response (obeys=6, localizes=5, withdraws=4, abnormal flexion=3, extensor response=2, none=1), and verbal response (oriented=5, confused=4, inappropriate=3, incomprehensible=2, none=1). Mild TBI (GCS 13-15) is in most cases a concussion and there is full neurological recovery, although many of these patients have short-term memory and concentration difficulties. In moderate TBI (GCS 9-13) the patient is lethargic or stuporous, and in severe injury (GCS 3-8) the patient is comatose, unable to open his or her eyes or follow commands.

Patients with severe TBI (comatose) have a significant risk of hypotension, hypoxaemia, and brain swelling. If these sequelae are not prevented or treated properly, they can exacerbate brain damage and increase the risk of death.

The term "traumatic intracerebral hemorrhage" as used herein refers to such bleeding that is caused, caused by, or associated with traumatic injury. Intracerebral hemorrhages commonly occur in the basal ganglia, thalamus, brain stem (predominantly the pons), cerebral hemispheres, and the cerebellum. Extension into the ventricles occurs in association with deep, large hematomas. Edematous parenchyma, often discolored by degradation products of hemoglobin, is visible adjacent to the clot. Histologic sections are characterized by the presence of edema, neuronal damage, macrophages, and neutrophils in the region surrounding the hematoma. The hemorrhage spreads between planes of white-matter cleavage, causing some destruction of the brain structure, and leaving intact neural tissue within and surrounding the hematoma.

Intraparenchymal bleeding results from the rupture of the small penetrating arterioles that originate from basilar arteries or from the anterior, middle, or posterior cerebral arteries. Degenerative changes in the arteriolar walls by chronic hypertension reduce compliance, weaken the wall, and increase the likelihood of spontaneous rupture. Studies suggest that most bleeding occurs at or near the bifurcation of affected arteries, where prominent degeneration of the tunica media and smooth muscles can be seen.

Neurological damage after TBI does not all occur immediately at the moment of impact (primary injury), but instead evolves afterwards (secondary injury). Secondary brain injury is the leading cause of in-hospital deaths after TBI. Most secondary brain injury is caused by brain swelling, with an increase in intracranial pressure and a subsequent decrease in cerebral perfusion leading to ischemia. Within hours of TBI, due to a breakdown of tight endothelial junctions which make up the blood-brain barrier, normally excluded intravascular proteins and fluid penetrate into cerebral parenchymal extracellular space (vasogenic edema). Once plasma constituents cross the BBB, the edema spreads. The vasogenic fluid accumulating in brain causes cerebral edema, raises intracranial pressure, and lowers the threshold of systemic blood pressure for cerebral ischemia. A reduction in cerebral blood flow or oxygenation below a threshold value or increased intracranial pressure leading to cerebral herniation increases brain damage and morbidity.

Although iron accumulation or iron overload in brain is commonly associated with neurodegenerative disorders such as Parkinson's and Alzheimer's diseases, and also plays a role in cellular damage following hemorrhagic stroke and traumatic brain injury. Despite the brain's highly regulated system for iron utilization and metabolism, these disorders often present following disruptions within iron metabolic pathways. Such dysregulation allows saturation of proteins involved in iron transport and storage, and may cause an increase in free ferrous iron within brain leading to oxidative damage. Not only do astrocytes, neurons, and brain endothelial cells serve unique purposes within the brain, but their individual cell types are equipped with distinct protective mechanisms against iron-induced injury [Gaasch J A, et al., Neurochem Res, 32(7):1196-208 (2007)].

Approximately 10% of TBI cases are complicated by intracerebral hemorrhage requiring surgery. The delay in the breakdown of the blood brain barrier and the development of cerebral edema after an intracerebral hemorrhage (ICH) suggest that there may be secondary mediators of both neural injury and edema. It generally is believed that blood and plasma products mediate most secondary processes that are initiated after an ICH.

Hypoxemia and hypotension occur before the patient reaches a hospital and significantly increase the risk of secondary brain injury and the likelihood of a poor outcome. Studies have reported that in children with TBI, 13% had a document hypoxemic (meaning having a decreased partial pressure of oxygen in the blood) episode and 6% had hypercapnia (meaning the condition of having an abnormally high level of carbon dioxide in the circulating blood). Various studies have reported that 27% to 55% of patients with TBI were hypoxemic (meaning causing hemoglobin oxygen saturation less than 90%) at the scene, in the ambulance, or on arrival at the emergency department. Intubation at the scene of the accident or in the emergency department was required for all patients if the GCS score was 3-5.73% if the GCS was 6-7, and 62% if the GCS was 8-9.

In adults, hypotension is defined as a single measurement of a systolic blood pressure below 90 mm Hg. Some studies have reported that hypotensive episodes were observed in 16% and 32% of patients with severe TBI at the time of hospital arrival and during surgical procedures, respectively. A single episode of hypotension was associated with increased morbidity and doubling of mortality. In children, a low systolic blood pressure, sustained for at least 5 minutes, is associated with a poor outcome.

Several pharmacological agents, such as free-radical scavengers, antagonists of N-methyl-D-aspartate, and calcium-channel blockers, have been studied in attempt to prevent the secondary injury associated with TBI, but none has proven effective.

There is a need to more accurately diagnose milder traumatic brain injuries with increasing awareness of the high prevalence in both military and civilian populations. Magnetic resonance imaging methods may be capable of detecting a number of the pathoanatomical and pathophysiological consequences of focal and diffuse traumatic brain injury. Susceptibility-weighted imaging (SWI) detects heme iron and reveals even small venous microhemorrhages occurring in diffuse vascular injury. Diffusion tensor imaging (DTI) reveals axonal injury by detecting alterations in water flow in and around injured axons. The overarching hypothesis of this paper is that newer, advanced MR imaging generates sensitive biomarkers of regional brain injury which allows for correlation with clinical signs and symptoms. [Benson R. R., et al., Neuro Rehabilitation, 31(3): 261-79 (2012)] https://www.ncbi.nlm.nih.gov/pubmed/23093454

Extracellular heme derived from hemoglobin following hemorrhage or released from dying cells induces the expression of heme oxygenase-1 (HO-1, HSP-32) which metabolizes heme to the gaseous mediator carbon monoxide (CO), iron (Fe) and biliverdin. Biliverdin and its product bilirubin are powerful antioxidants. Thus, expression of HO-1 is considered to be a protective mechanism against oxidative stress and has been described in microglia, astrocytes and neurons following distinct experimental models of pathological alterations to the brain such as subarachnoidal hemorrhage, ischemia and traumatic brain injury (TBI) and in human neurodegenerative diseases. [Beschorner R., et al., Aca Neuropathol, 100(4):377-84 (2000)]

Hypoxemia and hypotension commonly occur before the patient reaches a hospital and significantly increase the risk of secondary brain injury and the likelihood of a poor outcome. Studies have reported that in children with TBI, 13% had a documented hypoxemic (meaning having a decreased partial pressure of oxygen in the blood) episode and 6% had hypercapnia (meaning the condition of having an abnormally high level of carbon dioxide in the circulating blood). Various studies have reported that 27% to 55% of patients with TBI were hypoxemic (meaning causing hemoglobin oxygen saturation less than 90%) at the scene, in the ambulance, or on arrival at the emergency department. Intubation at the scene of the accident or in the emergency department was required for all patients if the GCS score was 3-5.73% if the GCS was 6-7, and 62% if the GCS was 8-9.

In adults, hypotension is defined as a single measurement of a systolic blood pressure below 90 mm Hg. Some studies have reported that hypotensive episodes were observed in 16% and 32% of patients with severe TBI at the time of hospital arrival and during surgical procedures, respectively. A single episode of hypotension was associated with increased morbidity and doubling of mortality. In children, a low systolic blood pressure, sustained for at least 5 minutes, is associated with a poor outcome.

2. Erythropoietin

Erythropoietin (hEPO), a 165 amino acid glycoprotein hormone, is the principal hormone involved in the regulation and maintenance of a physiological level of circulating erythrocyte mass. It is produced primarily by the kidney in the adult and by the liver during fetal life; and is maintained in the circulation at a concentration of about 15 mU/ml to about 20 mU/ml of serum, or about 0.01 nM under normal physiological conditions. EPO has been used extensively for the treatment of anemia in humans.

The hematopoietic effect of EPO is mediated by binding and inducing dimerization of two molecules of the EPO receptor (EpoR) on the cell surface [Watowich, S. S., et al., Mol Cell Biol, 14: 3535-49 (1994)]. The EpoR belongs to a cytokine receptor superfamily that is also related to the cytokines granulocyte colony-stimulating factor (G-CSF), granulocyte macrophage colony-stimulating factor (GM-CSF), interleukins 2-7 and ciliary neurotrophic factor (CNTF). The signaling pathway involves the autophosphorylation and activation of the Janus family protein tyrosine kinase, JAK-2, which further activates additional signaling proteins including STATS, Ras-mitogen-activated protein kinase (MAPK) and phosphatidylinositol 3-kinase (PI3K). Studies on structure activity relationships of EPO have identified regions and amino acids essential for binding to the erythropoietin receptor (EpoR) [Livnah, O., et al., Science, 273: 464-71 (1996); Wrighton, N. c., et al., Science, 273: 458-64 (1996); Wen, D., J Biol Chem, 269: 22839-46 (1994)].

In addition to its hematopoietic effects, studies have reported that EPO may have broad neuroprotective capabilities following CNS injury. [Brines, M. L., et al., Proc Natl Acad Sci USA, 97: 10526-31 (2000); Siren, A. L. and Ehrenreich, H., Eur Arch Psychiatry Clin Neurosci, 251: 179-84 (2001); Buemi, M., et al., 1. Neuropathol Exp Neurol, 62: 228-36 (2003); Li, w., et al., Ann Neurol, 56:767-77 (2004); Sakanaka, M., et al., Proc Natl Acad Sci USA, 95: 4635-40 (1998)]. Therapeutic effects of exogenously administered EPO on several diverse forms of neurologic injury, including occlusive cerebral vascular disease, acute brain trauma, epilepsy, and an autoimmune model of demyelinating disease, experimental autoimmune encephalomyelitis (EAE), have been tested and the degree of neurologic impairment was significantly reduced [Brines, M. L. et al., Proc Natl Acad Sci USA, 97: 10526-31 (2000); Li, W. et al., Ann Neurol, 56: 767-77 (2004); Tsai, P. T., et al., J Neurosci, 26: 1269-74 (2006); Buemi, M., et al., Clin Sci (Loud), 103: 275-82 (2002)]. Studies in which recombinant EPO and EPO mutants have been tested for their biological effects in a variety of animal models have suggested that the neuroprotection mediated by EPO might not occur through a conventional interaction between EPO and classic EpoR. The common receptor (cR) or CD131, which is also an important component for other ligands including IL-3, IL-5 and GM-CSF, has been proposed to be a key subunit associated with the EpoR that is responsible for EPO mediated non-hematopoietic effects. Additional unknown receptor(s) also may play critical roles in the non-hematopoietic effects induced by chemically modified or mutant EPO.

Long-term EPO therapy remains significantly limited in non-anemic patients with neurological injury because EPO treatment may overly stimulate erythropoiesis. To overcome this concern, EPO therapy would have to be limited to very short term use. Other EPO molecular preparations, such as an asialo-form of EPO, carbamylated EPO (CEPO), or certain EPO mutants, have been shown to be neuroprotective in animals following experimental traumatic spinal cord injury or acute stroke without provoking an increase in red blood cell mass [Erbayraktar, S., et al., Proc Natl Acad Sci USA, 100: 6741-46 (2003); Leist, M., et al., Science, 305: 239-42 (2004); MUL, K. C. and Golper, T. A. Blood Purif, 18: 13-17 (2000); Brines, M., et al., Proc Natl Acad Sci USA, 101: 14907-12 (2004)]. A short 17 amino acid EPO-derived linear peptide also was reported to have neuroprotective effects in cell culture, but it is in vivo biologic effects were not certain [Campana, W. M., et al., Int's J Mol Med, 1: 235-41 (1998)]. Taken all together, the evidence suggests that specific functional and structural domains may co-exist within the full 165 amino acid EPO molecule.

3. Neuroinflammatory Responses

Notwithstanding that the blood brain barrier tries to restrict and tightly control peripheral immune access to the CNS, the CNS is capable of dynamic immune and inflammatory responses to a variety of insults, including trauma. The acute neuroinflammatory response includes activation of microglia, appearance of dendritic cells, resident tissue macrophages in the CNS and the principle mediators of neuroinflammation, resulting in phagocytosis and the release of inflammatory mediators such as cytokines and chemokines chronic neuroinflammation includes long-standing activation of microglia and subsequent sustained release of inflammatory mediators, which works to perpetuate the inflammatory cycle, activating additional microglia, promoting their proliferation, and resulting in further release of inflammatory factors.

Iron is considered to be another redox-reactive metal ion that causes oxidative stress via the Fenton reaction. It is found to be elevated in many neurodegenerative diseases, such as AD, Parkinson's disease, and amyotrophic lateral sclerosis. [Kasarskis E J, et. al., Journal Neurologist Science, 130(2):203-8 (1995)].

Neurodegenerative CNS disorders, including, but not limited to, multiple sclerosis, Alzheimer's disease, Parkinson's disease, Huntington's disease, amyotrophic lateral sclerosis, are associated with chronic neuroinflammation.

DETAILED DESCRIPTION OF THE INVENTION

Glossary

The term "adjuvant" as used herein refers to any component which improves the characteristics, efficacy or potency of a formulation, drug, or immunological agent.

The term "administer" as used herein refers to dispensing, supplying, applying, giving, apportioning or contributing. The terms "administering" or "administration" are used interchangeably and include in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing the conventional nontoxic pharmaceutically acceptable carriers, adjuvants, and vehicles as desired, or may be locally administered by means such as, but not limited to, injection, implantation, grafting, topical application, or parenterally.

The term "topical administration" and "topically applying" as used herein are used interchangeably to refer to delivering a peptide, the nucleic acid, or a vector comprising the peptide or the nucleic acid onto one or more surfaces of a tissue or cell, including epithelial surfaces.

The term "topical" refers to administration of a composition at, or immediately beneath, the point of application. The phrase "topically applying" describes application onto one or more surfaces(s) including epithelial surfaces.

Topical administration, in contrast to transdermal administration, generally provides a local rather than a systemic effect. The terms "topical administration" and "transdermal administration" as used herein, unless otherwise stated or implied, are used interchangeably As used herein the phrase "pharmaceutically acceptable carrier" refers to any substantially non-toxic carrier useable for formulation and administration of the composition of the described invention in which the product of the described invention will remain stable and bioavailable. the pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition. The term "pharmaceutically-acceptable carrier" as used herein refers to one or more compatible solid or liquid filler, diluents or encapsulating substances which are suitable for administration to a human or other vertebrate animal.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation. The term "therapeutically effective amount" or an "amount effective" of one or more of the active agents of the present invention is an amount that is sufficient to provide a therapeutic effect. Generally, an effective amount of the active agents that can be employed according the described invention ranges from about 0.000001 mg/kg body weight to about 100 mg/kg body weight. However, dosage levels are based on a variety of factors, including the type of injury, the age, weight, sex, medical condition of the patient, the severity of the condition, the route of administration, and the particularly active agent employed. Thus, the dosage regimen may vary widely, but can be determined routinely by a physician using standard methods.

Pharmaceutical Composition for Treating TBI or Inflammatory Brain Disorders

According one aspect, the described invention provides a pharmaceutical composition for treating traumatic brain injury (TBI) or an inflammatory brain disease, disorder, or condition in a subject, the composition comprising:
1. a therapeutically effective amount of chromium III chloride, magnesium sulfate, thiamine, mineral oil, glyceryl stearate, propylene glycol; and
2. a pharmaceutically acceptable carrier.

Methods and pharmaceutical compositions are described herein that, inter alia, prevent, and/or treat neurologic complications such as cognitive, behavioral and/or physical impairment due to ischemia, neurodegeneration, trauma and metal poisoning.

In another aspect, under a representative embodiment of the invention, the possibility of an ischemic episode or neurodegeneration is recognized. The pharmaceutical compositions are administered transdermally to anywhere on human skin to bypass the liver system barrier and access the central nervous system directly through blood stream to avoid unwanted and potentially damaging side effects.

The pharmaceutical compositions include those substances such as chromium ITI chloride, hydroxypyridin-2-one or a hydroxamate residue as the iron-chelating function, Vitamin C, melatonin, alpha lipoic acid, chlorogenic acid, green tea extract, plant polyphenols, aspirin, N acetylcysteine, quercetin, EGCG, inositol, curcumin, and berin that may interact with iron chelators.

In view of its multifunctional roles, chromium compounds have been utilized in the treatment and improvement of neurodegenerative patients.

The following details a study that clearly demonstrates the clinical benefit of treatment of TBI with chromium III chloride 0.00169%.

The amount of chromium III chloride which may be used in the present invention ranges from about 0.000422 to 0.00169 percent by weight and preferably about 0.676 to 2.705 percent by weight of magnesium sulfate of the composition.

Chromium and magnesium sulfate are available commercially and are made by methods that are known to those of skill in the art. Additionally, chromium and magnesium compounds can be incorporated into solution, lotion, cream, ointment and gel formulations for transdermal application to the skin of patients with TBI or severe inflammatory brain disorder. In such transdermal formulations, concentrations from 0.000422% to 0.00169% by weight of chromium III chloride and 0.676% to 2.705% by weight of magnesium are incorporated into vehicle suitable for application to the skin. The resulting formulations are applied to the skin of TBI patients from 1 to 3 times daily.

Example 1

A clinical study of human subjects with TBI was carried out to show the effectiveness of the composition of the present invention in the treatment of TBI and inflammatory brain disorder. A fixed dose combination of lotion formulations containing chromium III chloride 0.000422% to 0.001695% by weight/total composition weight.

Compositions containing 0.5 mg by weight of chromium III chloride are administered at least once daily for 2 weeks to patients. At the end of the 2-week treatment period most patients will demonstrate a significant decrease in the activity of their inflammatory brain disorder. Formulations A, B, C and D (Table 1) were applied to each subject twice daily. Clinical appraisal was carried out at biweekly intervals.

TABLE 1

| Ingredient | % | | | |
|---|---|---|---|---|
| | A | B | C | D |
| Chromium III chloride | 0.000422 | 0.000844 | 0.00127 | 0.00169 |
| Magnesium | — | 1.352 | 2.028 | 2.705 |
| Thiamine mononitrate | — | — | ?? | ?? |

The results of the study are shown in Table 2 below:

TABLE 2

Clinical Evaluation of TBI Treatment

| Formulation | Evaluation Time (Weeks) | | | |
|---|---|---|---|---|
| | 1 | 2 | 4 | 6 |
| A | 0 | 2 | 2 | 3 |
| B | 1 | 2 | 3 | 4 |
| C | 2 | 3 | 4 | 4 |
| D | 2 | 4 | 4 | 4 |

0 = no response
1 = slight improvement
2 = good improvement
3 = very good improvement
4 = dramatic improvement The results of the foregoing tests show that chromium used in the systemic treatment of TBI (formulation A) is essentially ineffective as is the vehicle alone. However, the results of the foregoing tests shown a good improvement with magnesium sulfate and thiamine mononitrate (formulation B, C, and D).

Example 2

The study of Example 1 is repeated to show the efficacy and safety of the composition of the present invention in the treatment of TBI (Table 3). Safety and tolerability were assessed through evaluations of local tolerability and adverse events. At each visit, the investigator rated erythema, scaling, dryness, stinging/burning on a scale.

The efficacy variables were percent lesion count reduction from baseline (total, inflammatory, and non-inflammatory) and subject's assessment of TBI on a scale from 0 (marked improvement) to 5 (worse). Table 3 is a flow chart of assessed measurements during this study.

TABLE 3

| 1 | Marked Improvement |
|---|---|
| 2 | Moderated Improvement |
| 3 | Minimal Improvement |
| 4 | No Change |
| 5 | Worse |

Local tolerability measures of the signs and symptoms of skin irritation were considered adverse effects only if the severity of the expected signs and symptoms was such that an interruption of the subject's participation in the study, at his/her request or at the investigator's discretion, had occurred. Altered dosing regimens (such as every other day dosing) to manage irritation were not considered to be an interruption of the subject's participation in the study.

The results of the study are shown in Table 4 below.

TABLE 4

Efficacy and Safety Measurements

| Formulation | Evaluation Time (Weeks) | | | |
|---|---|---|---|---|
| | 1 | 2 | 4 | 6 |
| Efficacy | | | | |
| A | 4 | 3 | 3 | 2 |
| B | 3 | 3 | 2 | 1 |
| C | 3 | 2 | 1 | 1 |
| D | 3 | 2 | 1 | 1 |
| Safety | | | | |
| A | 4 | 3 | 3 | 2 |
| B | 3 | 3 | 2 | 2 |
| C | 3 | 2 | 1 | 1 |
| D | 2 | 1 | 1 | 1 |

As this was an open-label study, only descriptive data presentations were made. No formal statistical hypotheses were tested. Descriptive statistics were used to summarize all data.

Treatment with chromium, 0.00169 for up to 4 weeks showed continuing improvement in lesion counts (non-inflammatory, inflammatory and total) starting week 4. The greatest reductions in lesion counts were seen after 6 weeks of treatment.

Overall improvement was observed in the subject's assessment of TBI. The median assessment was "Moderated Improvement" at week 2, and "Marked Improvement" at week 4

In conclusion, chromium III chloride, 0.00169% was well-tolerated and effective in treatment of TBI patients.

Safety findings were consistent with the known profile of chromium. No unexpected, either systemic or dermatological, evidence of cumulative toxicity was observed over time. Consequently, extending treatment beyond 6 weeks does not suggest substantial additional risk for the subjects treated with chromium III chloride 0.000169%.

The efficacy of chromium III chloride 0.000169% was demonstrated for non-inflammatory, inflammatory brain disorder. Chromium III chloride 0.000169% showed continuing reductions greater than 95% for subjects treated for 6 weeks.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above described exemplary embodiments, but should be defined only in accordance with the following claims appended hereto and their equivalents.

For purposes of summarizing the invention, certain aspects, advantages, and novel features of the invention have been described herein. It is to be understood that not necessarily all such advantages may be achieved in accordance with anyone particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

It should be understood that the present invention is not limited to the embodiments disclosed, but is capable of numerous rearrangements, modifications, and substitutions of parts and elements without departing from the spirit of the invention.

What is claimed is:

1. A method for treating Alzheimer's disease, the method comprising:
    transdermally administering a pharmaceutical composition to the human body in need thereof, wherein the pharmaceutical composition comprising: from about 0.000422% to about 0.00169% by weight of chromium chloride; from about 0.676% to about 2.705% by weight of magnesium sulfate; and therapeutically effective amount of thiamine mononitrate, vitamin B12, and vitamin D3, wherein the percentage by weight is relative to the total weight of the composition.

2. The method according to claim 1, wherein the method further comprises reducing infiltration of a population of a mononuclear cell into the brain of the subject.

3. The method according to claim 1 comprising administering said composition for at least two (2) weeks.

4. The method of claim 1, comprising administering said composition for at least four (4) weeks.

5. The method of claim 1, comprising administering said composition for at least six (6) weeks.

6. The method of claim 1, comprising administering said composition at least once every day.

7. The method of claim 1, wherein said composition is selected from a group consisting of lotion, gel, and any combination thereof.

* * * * *